(12) United States Patent
Tsuchida

(10) Patent No.: US 9,156,864 B2
(45) Date of Patent: Oct. 13, 2015

(54) HYDROSILYLATION METHOD, METHOD FOR PRODUCING ORGANOSILICON COMPOUND, AND ORGANOSILICON COMPOUND

(71) Applicant: SHIN-ETSU CHEMICAL CO., LTD., Chiyoda-ku, Tokyo (JP)

(72) Inventor: Kazuhiro Tsuchida, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/574,049

(22) Filed: Dec. 17, 2014

(65) Prior Publication Data

US 2015/0105576 A1  Apr. 16, 2015

Related U.S. Application Data

(62) Division of application No. 13/314,408, filed on Dec. 8, 2011, now Pat. No. 8,946,464.

(30) Foreign Application Priority Data

Dec. 9, 2010 (JP) ................................. 2010-274710
Dec. 9, 2010 (JP) ................................. 2010-274730
Dec. 9, 2010 (JP) ................................. 2010-274745

(51) Int. Cl.
*C07F 7/08* (2006.01)
*C07F 7/18* (2006.01)

(52) U.S. Cl.
CPC ................. *C07F 7/18* (2013.01); *C07F 7/0801* (2013.01); *C07F 7/0809* (2013.01); *C07F 7/0879* (2013.01); *C07F 7/188* (2013.01)

(58) Field of Classification Search
USPC .......................................... 556/478, 479, 481
See application file for complete search history.

(56) References Cited

U.S. PATENT DOCUMENTS

| | | | |
|---|---|---|---|
| 4,736,049 A | 4/1988 | Suzuki et al. | |
| 4,855,498 A | 8/1989 | Roat et al. | |
| 5,986,124 A | 11/1999 | Tachikawa et al. | |
| 6,048,994 A | 4/2000 | Tachikawa et al. | |
| 6,326,506 B1 | 12/2001 | Tachikawa et al. | |
| 6,365,696 B1 * | 4/2002 | Westmeyer et al. | 528/12 |
| 6,590,117 B1 | 7/2003 | Westmeyer et al. | |
| 8,039,646 B2 | 10/2011 | Bade et al. | |
| 2003/0100784 A1 | 5/2003 | Giessler et al. | |
| 2008/0103324 A1 | 5/2008 | Pevere et al. | |
| 2010/0056745 A1 | 3/2010 | Pevere et al. | |

FOREIGN PATENT DOCUMENTS

| | | |
|---|---|---|
| EP | 0 472 438 A1 | 2/1992 |
| EP | 1 266 903 A1 | 12/2002 |
| EP | 2 194 060 A1 | 6/2010 |
| JP | 63-33384 A | 2/1988 |
| JP | 2-191287 A | 7/1990 |
| JP | 4-103588 A | 4/1992 |
| JP | 4-128292 A | 4/1992 |
| JP | 5-286985 A | 11/1993 |
| JP | 8-27165 A | 1/1996 |
| JP | 8-311079 A | 11/1996 |
| JP | 11-29584 A | 2/1999 |
| JP | 11-71385 A | 3/1999 |
| JP | 11-180986 A | 7/1999 |
| JP | 2000-143679 A | 5/2000 |
| JP | 2001-247581 A | 9/2001 |
| JP | 2001-335589 A | 12/2001 |
| JP | 2003-516996 A | 5/2003 |
| JP | 2003-313193 A | 11/2003 |
| JP | 2005-42050 A | 2/2005 |
| JP | 2005-509684 A | 4/2005 |
| JP | 2007-513930 A | 5/2007 |
| JP | 2010-1255 A | 1/2010 |
| JP | 2010-518031 A | 5/2010 |

OTHER PUBLICATIONS

European Search Report dated May 24, 2013 of Application No. 11 19 1686.
Extended European Search Report dated Apr. 4, 2012, issued in European Patent Application No. 11191686.2.
Voronkov et al., "The Catalytic Reactions of Triethyl- and Triethoxy-Silane with Unsaturated Sulphides", Journal of Organometallic Chemistry, 190, 1980, pp. 335-341.
Yoshino et al., "Synthesis of a silane coupling agent containing a 4-(perfluoroalkyl)phenyl group and its application to the surface modification of glass", Journal of Fluorine Chemistry, 71, 1995, pp. 21-29.

* cited by examiner

*Primary Examiner* — Sudhakar Katakam
*Assistant Examiner* — Pancham Bakshi
(74) *Attorney, Agent, or Firm* — Birch Stewart Kolasch & Birch, LLP

(57) ABSTRACT

A hydrosilylation method is provided. In this hydrosilylation method, silylation of the carbon atom other than the terminal carbon atom and generation of the by-product isomer by internal migration of the double bond are suppressed without sacrificing the hydrosilylation reactivity, even if an olefin compound having tertiary amine atom which can be a catalyst poison was used. In the hydrosilylation, an olefin compound having carbon-carbon unsaturated bond, and a compound having hydrogensilyl group are reacted in the presence of an acid amide compound, a nitrile compound and an aromatic hydroxyl compound, or an organoamine salt compound, by using catalytic action of platinum and/or its complex compound.

6 Claims, No Drawings

HYDROSILYLATION METHOD, METHOD FOR PRODUCING ORGANOSILICON COMPOUND, AND ORGANOSILICON COMPOUND

CROSS-REFERENCE TO RELATED APPLICATION

The present application is a 37 C.F.R. §1.53(b) divisional of, and claims priority to, U.S. application Ser. No. 13/314,408, filed Dec. 8, 2011. Priority is also claimed to Japanese Patent Application No. 2010-274710 filed Dec. 9, 2010, Japanese Patent Application No. 2010-274730 filed Dec. 9, 2010 and Japanese Patent Application No. 2010-274745 filed Dec. 9, 2010. The entire contents of each of these applications are hereby incorporated by reference.

TECHNICAL FIELD

This invention relates to a hydrosilylation method having excellent reaction activity and excellent selectivity of the addition position. This invention also relates to a method for producing an organosilicon compound using such method, and an organosilicon compound produced by such methods.

BACKGROUND ART

The hydrosilylation in which a compound having vinyl group and a compound having hydrogen atom bonded to the silicon atom are reacted in the presence of a platinum catalyst for addition of both compounds is a technology well known in the art for synthesis and modification of an organosilane or an organopolysiloxane and silylation of an organic compound or an organic high molecular weight molecule.

Production method of a compound having a hydrogencarbonoxysilyl group such as an alkoxysilyl group may be divided into the following two categories.

First Method

A method wherein an aliphatic unsaturated organic compound is hydrosilylated by using a hydrogenchlorosilane compound, and then converting the chlorosilyl group into an alkoxysilyl group by using an alcohol.

Second Method

A method wherein an aliphatic unsaturated organic compound is hydrosilylated by using a hydrogenalkoxysilane compound.

Of these two methods, the procedure of the second method is more convenient, and the second method is also superior in the productivity in view of the smaller amount of ionic impurities and waste generated in the alkoxylation. However, the hydrogenalkoxysilane compound is inferior to the hydrogenchlorosilane compound in the hydrosilylation activity, and it was also a material with low selectivity of the addition site since migration of the double bond in the unsaturated organic compound was promoted.

As a method for improving reactivity of the hydrosilylation and controlling the addition site by suppressing the migration of the double bond in a system using a hydrogenalkoxysilane, JP-A 2000-143679 and JP-A H11-180986 propose a method for hydrosilylating a hydrogenalkoxysilane and an aliphatic unsaturated organic compound or a vinyl-substituted aromatic compound by using a platinum catalyst in the presence of a carboxylic acid compound. However, in these methods, sufficient control of the addition selectivity was not realized, and regulation of the generation of the side product from the carboxylic acid by transesterification as well as adjustment of an amount added was difficult. In addition, hydrosilylation reactivity with the unsaturated organic compound containing tertiary amine atom, for example, allyl isocyanate or triallyl isocyanurate was still insufficient in these technologies.

As a matter of course, improvement of the hydrosilylation reactivity leads to the improvement of the reaction yield, and hence, improvement of the production efficiency. An organosilicon compound having its terminal carbon atom hydrosilylated exhibits higher performance than its isomers which has been silylated at a position other than its terminal when it is used as a coupling agent or a modifying agent. In the case of an organopolysiloxane, various physical properties including heat resistance are superior compared to the isomers. Accordingly, a hydrosilylation method capable of producing an organosilicon compound having a hydrosilylated terminal at a high yield and high selectivity has been awaited.

SUMMARY OF THE INVENTION

The present invention has been completed in view of the situation as described above, and an object of the present invention is to provide a hydrosilylation method which exhibits high reaction activity even when an olefin compound having tertiary amine atom which can be a catalyst poison is used, and wherein silylation of the carbon atom other than the terminal carbon atom and generation of the by-product isomer by internal migration of the double bond is suppressed. Another object of the present invention is to provide a method for producing an organosilicon compound using this method, and an organosilicon compound produced by such method.

The inventor of the present invention made an intensive study to attain the objects as described above, and found that, when (i) an olefin compound having carbon-carbon unsaturated bond and (ii) a compound having hydrogensilyl group are hydroxylated in the presence of platinum and/or its complex compound using an acid amide compound, a nitrile compound and an aromatic hydroxy compound, or an organoamine salt compound for the reaction aid, the hydrosilylation can be conducted without sacrificing reactivity of the hydrosilylation while suppressing silylation of the carbon atom other than the terminal carbon atom and generation of the by-product isomer by internal migration of the double bond, even if an olefin compound having tertiary amine atom was used.

Accordingly, the present invention provides the hydrosilylation method, the method for producing an organosilicon compound using such method, and the organosilicon compound as described below.

(1) A hydrosilylation method wherein
(i) an olefin compound having carbon-carbon unsaturated bond, and
(ii) a compound having hydrogensilyl group are reacted in the presence of an acid amide compound by using catalytic action of platinum and/or its complex compound.

(2) A hydrosilylation method according to the above (1) wherein the acid amide compound is represented by the following general formula (1):

wherein $R^0$ is hydrogen atom or a k-valent hydrocarbon group containing 1 to 30 carbon atoms, $R^1$ is independently hydrogen atom or a monovalent hydrocarbon group containing 1 to 20 carbon atoms, and k is 1 or 2.

(3) A hydrosilylation method according to the above (1) or (2) wherein the acid amide compound is a primary acid amide compound represented by the following general formula (2):

$$R^2—C(=O)—NH_2 \quad (2)$$

wherein $R^2$ is hydrogen atom or a monovalent hydrocarbon group containing 1 to 30 carbon atoms.
(4) A hydrosilylation method wherein
  (i) an olefin compound having carbon-carbon unsaturated bond, and
  (ii) a compound having hydrogensilyl group are reacted in the presence of a nitrile compound and an aromatic hydroxyl compound by using catalytic action of platinum and/or its complex compound.
(5) A hydrosilylation method according to the above (4) wherein the nitrile compound is a member selected from acetonitrile, acrylonitrile, propane nitrile, butane nitrile, and benzonitrile, and the aromatic hydroxyl compound is a member selected from phenol, hydroquinone, cresol, and bisphenol A.
(6) A hydrosilylation method wherein
  (i) an olefin compound having carbon-carbon unsaturated bond, and
  (ii) a compound having hydrogensilyl group are reacted in the presence of an organoamine salt compound by using catalytic action of platinum and/or its complex compound.
(7) A hydrosilylation method according to the above (6) wherein the organoamine salt compound is an organoammonium salt compound represented by the following general formula (5):

$$R^5—[C(=O)O^-.NR^6_4{}^+]_h \quad (5)$$

wherein $R^5$ is an h-valent hydrocarbon group containing 1 to 20 carbon atoms, $R^6$ is independently hydrogen atom or a monovalent hydrocarbon group containing 1 to 6 carbon atoms, and h is 1 or 2.
(8) A hydrosilylation method according to any one of the above (1) to (7) wherein the compound having a hydrogensilyl group is a hydrogenorganoxysilane represented by the following general formula (3):

$$H—SiR^3{}_nX_{3-n} \quad (3)$$

wherein $R^3$ is a monovalent hydrocarbon group, X is an organoxy group, and n is an integer of 0 to 2; or a hydrolytic condensation product obtained by using the hydrogenorganoxysilane as at least one of its constitutional component.
(9) A hydrosilylation method according to the above (8) wherein X in the general formula (3) is methoxy group, ethoxy group, or 2-propenoxy group.
(10) A hydrosilylation method according to the above (9) wherein the compound containing a hydrogensilyl group is selected from hydrogentrimethoxysilane, hydrogenmethyldimethoxysilane, hydrogendimethylmethoxysilane, hydrogentriethoxysilane, hydrogenmethyldiethoxysilane, hydrogendimethylethoxysilane, hydrogentri(2-propenoxy)silane, hydrogenmethyldi(2-propenoxy)silane, hydrogendimethyl(2-propenoxy)silane, organopolysiloxane and organosilsesquioxane having hydrosilyl group produced by hydrolytic condensation of such silane monomer, 1,3,5,7-tetramethyltetrasiloxan, 1,1,3,3-tetramethyldisiloxane, pentamethyldisiloxane, and dimethyl silicone polymer containing 3 to 100 silicon atoms having hydrosilyl group on its side chain or at its terminal.
(11) A hydrosilylation method according to any one of the above (1) to (10) wherein the olefin compound is selected from an olefin compound containing tertiary amine atom; a diene compound represented by the following general formula (4):

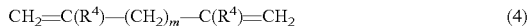

$$CH_2=C(R^4)—(CH_2)_m—C(R^4)=CH_2 \quad (4)$$

wherein $R^4$ is independently hydrogen atom or a monovalent hydrocarbon group, and m is an integer of 0 to 20; and a compound containing an aliphatic ring structure and/or an aromatic ring structure having vinyl group or allyl group.
(12) A hydrosilylation method according to the above (11) wherein the olefin compound is selected from allyl isocyanate, triallyl isocyanurate, 1,3-butadiene, isoprene, 1,4-pentadiene, 1,5-hexadiene, 1,6-heptadiene, 1,7-octadiene, 1,8-nonadiene, 1,9-decadiene, divinylcyclohexane, trivinylcyclohexane, diallylcyclohexane, triallylcyclohexane, styrene, allyl benzene, and allyl phenol.
(13) A method for producing an organosilicon compound wherein the method uses a hydrosilylation method according to any one of the above (1) to (12).
(14) An organosilicon compound produced by the production method of the above (13).

Advantageous Effects of the Invention

The present invention has enabled a highly reactive hydrosilylation method wherein the hydrosilylation can be conducted without sacrificing reactivity of the hydrosilylation while suppressing silylation of the carbon atom other than the terminal carbon atom and generation of the by-product isomer by internal migration of the double bond, even if an olefin compound having tertiary amine atom which can be a catalyst poison was used.

DESCRIPTION OF THE EMBODIMENTS

The hydrosilylation method of the present invention is a method wherein (i) an olefin compound having carbon-carbon unsaturated bond, and (ii) a compound having hydrogensilyl group are reacted in the presence of an acid amide compound, a nitrile compound and an aromatic hydroxyl compound, or an organoamine salt compound, by using catalytic action of platinum and/or its complex compound.

Next, the present invention is described in detail.

First, the starting materials used in the method of the present invention are described.

(i) Olefin Compound Having Carbon-Carbon Unsaturated Bond

The olefin compound used in the present invention is not particularly limited as long as it is a compound having carbon-carbon double bond as typically represented by vinyl group. Among these, use of an olefin compound having tertiary amine atom; diene compound represented by the following general formula (4):

$$CH_2=C(R^4)—(CH_2)_m—C(R^4)=CH_2 \quad (4)$$

wherein $R^4$ is independently hydrogen atom or a monovalent hydrocarbon group, m is an integer of 0 to 20; a compound having an aliphatic ring structure and/or an aromatic ring structure having vinyl group or allyl group for the substrate of the hydrosilylation is remarkably advantageous.

In the formula (4), $R^4$ is independently hydrogen atom or a monovalent hydrocarbon group containing 1 to 10 carbon atoms, and preferably 1 to 6 carbon atoms such as methyl group, ethyl group, propyl group, hexyl group, cyclohexyl group; and m is an integer of 0 to 20, and preferably 2 to 10.

Non-limited examples of the olefin compound include allyl isocyanate, triallyl isocyanurate; 1,3-butadiene, isoprene, 1,4-pentadiene, 1,5-hexadiene, 1,6-heptadiene, 1,7-octadiene, 1,8-nonadiene, 1,9-decadiene; divinylcyclohexane, trivinylcyclohexane, diallylcyclohexane, triallylcyclohexane, styrene, allyl benzene, and allyl phenol.

(ii) Compound Having Hydrogensilyl Group

The compound having hydrogensilyl group used in the present invention is preferably a hydrogenorganoxysilane represented by the following general formula (3):

$$H\!-\!SiR^3{}_nX_{3-n} \tag{3}$$

wherein $R^3$ is a monovalent hydrocarbon group, X is an organoxy group, n is an integer of 0 to 2; or a hydrolytic condensate produced by using this hydrogenorganoxysilane as at least one constituent. $R^3$ is not particularly limited as long as it is a monovalent hydrocarbon group containing 1 to 10 carbon atoms, and preferably 1 to 6 carbon atoms. However, $R^3$ is preferably an alkyl group such as methyl group, ethyl group, or propyl group, or an aryl group such as phenyl group, and the most preferred is methyl group. X is not particularly limited as long as it is an organoxy group. However, X is preferably an alkoxy group such as methoxy group or ethoxy group or an alkenoxy group such as 2-propenoxy group in view of the availability of the availability. The hydrolytic condensate produced by using this hydrogenorganoxysilane as at least one constituent may contain other constituents, and such constituent may be an organosilicon compound having an alkoxysilyl group (such as methyl group, ethyl group, and propyl group), and the resulting condensate is not particularly limited for its polymer structure, and it may have straight chain, branched, cyclic, or other structure.

Non-limiting examples include hydrogentrimethoxysilane, hydrogenmethyldimethoxysilane, hydrogendimethylmethoxysilane, hydrogentriethoxysilane, hydrogenmethyldiethoxysilane, hydrogendimethylethoxysilane, hydrogentri(2-propenoxy)silane, hydrogenmethyldi(2-propenoxy) silane, hydrogendimethyl(2-propenoxy)silane, an organopolysiloxane having hydrosilyl group produced by hydrolytic condensation of such silane monomer, organosilsesquioxane, a cyclic siloxane having a hydrosilyl group such as 1,3,5,7-tetramethyltetrasiloxan, 1,1,3,3-tetramethyldisiloxane, pentamethyldisiloxane, dimethyl silicone polymer containing 3 to 100 silicon atoms having hydrosilyl group on its side chain or terminal.

The compound having a hydrogensilyl group (ii) may be used at an amount of 0.7 to 1.5 mol, and more preferably 0.9 to 1.1 mol in relation to 1 mol of the unsaturated group of the olefin compound (i).

Hydrosilylation Catalyst

The hydrosilylation catalyst used in the present invention is platinum (Pt) and/or a complex compound having the central metal of the platinum (Pt), which is known in the art. Examples include alcohol solution of chloroplatinic acid; 1,3-divinyltetramethyldisiloxane complex of chloroplatinic acid and a compound obtained by neutralizing the complex; and 1,3-divinyltetramethyldisiloxane complex wherein oxidation number of the central metal is Pt(II) or Pt(0). The preferred are the complex other than those having the oxidation number of the central metal of Pt(IV) in view of the selectivity of the addition site, and the most preferred are those with the oxidation number of Pt(0) or Pt(II).

Amount of the hydrosilylation catalyst used in the present invention is not particularly limited as long as it is a catalytic amount for the hydrosilylation. The hydrosilylation catalyst is preferably used at 0.000001 to 1 mol, and more preferably 0.0001 to 0.01 mol in relation to 1 mol of the olefin compound (i). Sufficient catalytic effects may not be realized when used at less than 0.000001 mol, while the effect is saturated at an amount in excess of 1 mol, and such addition may result in the high production cost and economic disadvantage.

Acid Amide Compound

The acid amide compound which is a hydrosilylation aid used in the present invention is not particularly limited as long as it is a carboxylic acid amide compound comprising a carboxylic acid and an amine represented by the following general formula (1):

$$R^0\!-\![C(\!=\!O)\!-\!NR^1{}_2]_k \tag{1}$$

wherein $R^0$ is hydrogen atom or a k-valent hydrocarbon group containing 1 to 30 carbon atoms, $R^1$ is independently hydrogen atom or a monovalent hydrocarbon group containing 1 to 20 carbon atoms, and k is 1 or 2. However, in view of the cost effectiveness, the preferred is a primary acid amide compound represented by the following general formula (2):

$$R^2\!-\!C(\!=\!O)\!-\!NH_2 \tag{2}$$

wherein $R^2$ is hydrogen atom or a monovalent hydrocarbon group containing 1 to 30 carbon atoms.

In the formulae (1) and (2), $R^0$ is hydrogen atom or a k-valent hydrocarbon group containing 1 to 30 carbon atoms, and preferably 1 to 20 carbon atoms, $R^2$ is hydrogen atom or a monovalent hydrocarbon group containing 1 to 30 carbon atoms, and preferably 1 to 20 carbon atoms. When the $R^0$ and $R^2$ are independently a monovalent groups, exemplary non-limited groups include alkyl groups such as methyl group, ethyl group, propyl group, isopropyl group, butyl group, hexyl group, pentadecyl group, and heptadecyl group, cycloalkyl groups such as cyclohexyl group, aryl groups such as phenyl group, and alkenyl groups such as vinyl group. When the $R^1$ is a divalent group, non-limited exemplary groups include alkylene groups such as methylene group, ethylene group, and propylene group, alkenylene groups such as vinylene group, and arylene groups such as phenylene group. $R^1$ is independently hydrogen atom or a monovalent hydrocarbon group containing 1 to 20 carbon atoms, and preferably 1 to 6 carbon atoms, and non-limiting examples include alkyl groups such as methyl group, ethyl group, propyl group, isopropyl group, butyl group, and hexyl group, cycloalkyl groups such as cyclohexyl group, and aryl groups such as phenyl group.

Exemplary acid amide compounds include formamide, acetamide, N-methylacetamide, N,N-dimethylacetamide, propionamide, acrylamide, malonamide, succinamide, maleamide, fumaramide, benzamide, phthalamide, palmitamide, and stearamide, which are commercially available. In view of the availability and effectiveness as a hydrosilylation aid, the preferred are formamide, acetamide, benzamide, and stearamide.

Amount of the acid amide compound used in the present invention is not particularly limited as long as the intended silylation aid effects (promotion of the reaction and improvement of the selectivity) are realized. However, the acid amide compound is preferably used at 0.00001 to 10 mol, and more preferably at 0.001 to 1 mol in relation to 1 mol of the olefin compound (i). Sufficient catalytic effect may not be achieved when used at less than 0.00001 mol while the catalytic activity is saturated at an amount in excess of 10 mol. Such excessive use may also result in the loss of catalytic activity.

Nitrile Compound

Examples of the nitrile compound which is a hydrosilylation aid used in the present invention include acetonitrile, acrylonitrile, propanenitrile, butanenitrile, and benzonitrile. In view of the availability and effectiveness as a hydrosilylation aid, the preferred is acetonitrile.

Amount of the nitrile compound used in the present invention is not particularly limited as long as the intended silylation aid effects (promotion of the reaction and improvement of the selectivity) are realized. However, the nitrile compound is preferably used at 0.00001 to 20 mol, and more preferably at 0.001 to 10 mol in relation to 1 mol of the olefin compound (i). Sufficient catalytic effect may not be achieved when used at less than 0.00001 mol while the effect is saturated at an amount in excess of 20 mol, and this may result in the loss of productivity.

Aromatic Hydroxy Compound

The aromatic hydroxy compound which is a hydrosilylation aid used in the present invention is used with the nitrile compound as described above, and examples include phenol, hydroquinone, cresol, and bisphenol A, which are commercially available. In view of the availability and effectiveness as a hydrosilylation aid, the preferred is phenol.

Amount of the aromatic hydroxy compound used in the present invention is not particularly limited as long as the intended silylation aid effects (promotion of the reaction and improvement of the selectivity) are realized. However, the nitrile compound is preferably used at 0.00001 to 10 mol, and more preferably at 0.001 to 10 mol in relation to 1 mol of the olefin compound (i). Sufficient catalytic effect may not be achieved when used at less than 0.00001 mol while the effect is saturated at an amount in excess of 10 mol, and this may result in the loss of productivity.

In the present invention, the nitrile compound (NC) and the aromatic hydroxy compound (AHC) are used at a molar ratio ((NC)/(AHC)) of 1 to 100, preferably 10 to 80, and more preferably 20 to 60. When the molar ratio is less than 1, the selectivity may not be sufficiently realized, and also, when the compound having hydrogensilyl group used for the starting material contains an alkoxysilyl group, such low ratio may result in the increased risk of transesterification, and hence, in the reduced yield. The silylation aid effects (promotion of the reaction and improvement of the selectivity) may not be sufficiently realized when the molar ratio is higher than 100.

Organoamine Salt Compound

The organoamine salt compound which is a hydrosilylation aid used in the present invention is not particularly limited as long as it is an organoamine salt compound produced by (acid-base) salt formation reaction of an organic acid (which is typically a carboxylic acid) and an amine (which is typically ammonia). However, in view of the cost effectiveness, the organoamine salt compound is most preferably an organoammonium salt compound represented by the following general formula (5):

$$R^5-[C(=O)O^-.NR^6_4{}^+]_h \quad (5)$$

wherein $R^5$ is an h-valent hydrocarbon group containing 1 to 20 carbon atoms, $R^6$ is independently hydrogen atom or a monovalent hydrocarbon group containing 1 to 6 carbon atoms, and h is 1 or 2.

In the formula (5), $R^5$ is an h-valent hydrocarbon group containing 1 to 20 carbon atoms, and preferably 1 to 10 carbon atoms. When $R^5$ is a monovalent group, non-limited exemplary groups include alkyl groups such as methyl group, ethyl group, propyl group, isopropyl group, butyl group, and hexyl group, cycloalkyl groups such as cyclohexyl group, and aryl groups such as phenyl group, and alkenyl groups such as vinyl group, and when $R^5$ is a divalent group, non-limited exemplary groups include alkylene groups such as methylene group, ethylene group, and propylene group, alkenylene groups such as vinylene group, and arylene groups such as phenylene group. $R^6$ is independently hydrogen atom or a monovalent hydrocarbon group containing 1 to 6 carbon atoms, for example, an alkyl group such as methyl group, ethyl group, or propyl group.

Exemplary organoamine salt compounds include ammonium acetate, methylamine acetate, dimethylamine acetate, trimethylamine acetate, ethylamine acetate, diethylamine acetate, triethylamine acetate, ammonium propionate, ammonium benzoate, ammonium acrylate, ammonium malonate, ammonium maleate, ammonium fumarate, and ammonium phthalate, which are commercially available. In view of the availability and effectiveness as a hydrosilylation aid, the preferred are ammonium acetate and ammonium propionate.

Amount of the organoamine salt compound used in the present invention is not particularly limited as long as the intended silylation aid effects (promotion of the reaction and improvement of the selectivity) are realized. However, the organoamine salt compound is preferably used at 0.00001 to 10 mol, and more preferably at 0.001 to 1 mol in relation to 1 mol of the olefin compound (i). Sufficient catalytic effect may not be achieved when used at less than 0.00001 mol while the effect is saturated at an amount in excess of 10 mol, and this may result in the loss of productivity.

In conducting the production method of the present invention, the reaction temperature is preferably 50 to 150° C., more preferably 60 to 130° C., and still more preferably 70 to 110° C. The reaction temperature of less than 50° C. may result in the low reaction rate, and hence, low production efficiency. The reaction temperature in excess of 150° C. results in the difficulty of regulating the addition site, and hence, generation of the addition isomer as well as the risk of side reaction such as dehydrogenation caused by the hydrosilyl group. The reaction time is preferably 10 to 300 minutes, and more preferably 60 to 120 minutes.

If necessary, the production method of the present invention may be conducted by using a solvent. The solvent used is not particularly limited as long as the solvent does not inhibit the reaction and the solvent is not reactive with the starting materials. Typical solvents include alcohol solvents, ether solvents, hetero atom-containing polar solvents, and hydrocarbon solvents, and examples include alcohol solvents such as methanol, ethanol, and propanol, ether solvents such as diethylether, dimethoxy ethane, and tetrahydrofuran, hetero atom-containing solvents such as acetonitrile and dimethylformamide, aliphatic hydrocarbon compounds such as hexane and heptane, and aromatic hydrocarbon compounds such as toluene and xylene, which may be used alone or in combination of two or more.

EXAMPLES

Next, the present invention is described in further detail by referring to Examples and Comparative Examples which by no means limit the scope of the present invention. In the following Examples and Comparative Examples, "parts" means parts by weight.

In the following Examples and Comparative Examples, compositional analysis of the reaction product was conducted by gas chromatography with thermal conductivity-type detector, and by comparing with the standard compound that had been identified by NMR analysis.

The hydrosilylation conversion rate is the proportion of the compound consumed in the reaction in relation to the amount of the compound containing hydrogensilyl group that had been charged, which was calculated by gas chromatography.

The platinum complex used was toluene solution of the 0 valent platinum complex of divinyl siloxane. The addition isomer in the Examples is a compound in which silyl addition occurred at the carbon atom other than the olefin terminal carbon atom.

Example 1

A 500 ml separable flask equipped with a stirrer, a reflux condenser, a dropping funnel, and a thermometer was charged with 24.9 parts (0.1 mol) of triallyl isocyanurate, 0.11 part (0.002 mol) of acetamide, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 36.7 parts (0.3 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 80° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 1.

Example 2

The procedure of Example 1 was repeated except that the trimethoxysilane which was a starting material was replaced with triethoxysilane. The conversion rate and the production rate of the addition isomer are shown in Table 1.

Example 3

The procedure of Example 1 was repeated except that the trimethoxysilane which was a starting material was replaced with pentamethyldisiloxane. The conversion rate and the production rate of the addition isomer are shown in Table 1.

Example 4

A 500 ml separable flask equipped with a stirrer, a reflux condenser, a dropping funnel, and a thermometer was charged with 82.0 parts (1 mol) of 1,5-hexadiene, 0.77 part (0.013 mol) of acetamide, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 244.4 parts (2 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 70° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 2.

Example 5

The procedure of Example 4 was repeated except that the trimethoxysilane which was a starting material was replaced with triethoxysilane. The conversion rate and the production rate of the addition isomer are shown in Table 2.

Example 6

The procedure of Example 4 was repeated except that the trimethoxysilane which was a starting material was replaced with pentamethyldisiloxane. The conversion rate and the production rate of the addition isomer are shown in Table 2.

Example 7

A 500 ml separable flask equipped with a stirrer, a reflux condenser, a dropping funnel, and a thermometer was charged with 104.0 parts (1 mol) of styrene, 0.77 part (0.013 mol) of acetamide, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 122.2 parts (1 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 70° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 3.

Example 8

The procedure of Example 7 was repeated except that the trimethoxysilane which was a starting material was replaced with triethoxysilane. The conversion rate and the production rate of the addition isomer are shown in Table 3.

Example 9

The procedure of Example 7 was repeated except that the trimethoxysilane which was a starting material was replaced with pentamethyldisiloxane. The conversion rate and the production rate of the addition isomer are shown in Table 3.

Comparative Example 1

The procedure of Example 1 was repeated except that the acetamide was not used. The conversion rate and the production rate of the addition isomer are shown in Table 1.

Comparative Example 2

The procedure of Example 1 was repeated except that the acetamide was replaced with acetic acid. The conversion rate and the production rate of the addition isomer are shown in Table 1.

Comparative Example 3

The procedure of Example 4 was repeated except that the acetamide was not used. The conversion rate and the production rate of the addition isomer are shown in Table 2.

Comparative Example 4

The procedure of Example 4 was repeated except that the acetamide was replaced with acetic acid. The conversion rate and the production rate of the addition isomer are shown in Table 2.

Comparative Example 5

The procedure of Example 7 was repeated except that the acetamide was not used. The conversion rate and the production rate of the addition isomer are shown in Table 3.

Comparative Example 6

The procedure of Example 7 was repeated except that the acetamide was replaced with acetic acid. The conversion rate and the production rate of the addition isomer are shown in Table 3.

TABLE 1

|  | Conversion rate | Production rate of the addition isomer |
| --- | --- | --- |
| Example 1 | 98.1% | 0.8% |
| Example 2 | 98.3% | 0.7% |
| Example 3 | 98.8% | 0.3% |
| Comparative Example 1 | 35.3% | 1.6% |
| Comparative Example 2 | 86.6% | 5.6% |

TABLE 2

|  | Conversion rate | Production rate of the addition isomer |
| --- | --- | --- |
| Example 4 | 91.7% | 0.9% |
| Example 5 | 89.1% | 0.8% |
| Example 6 | 90.2% | 0.5% |
| Comparative Example 3 | 43.2% | 9.6% |
| Comparative Example 4 | 76.5% | 1.5% |

TABLE 3

|  | Conversion rate | Production rate of the addition isomer |
| --- | --- | --- |
| Example 7 | 93.2% | 0.6% |
| Example 8 | 88.3% | 0.3% |
| Example 9 | 92.1% | 0.8% |
| Comparative Example 5 | 1.6% | 0.9% |
| Comparative Example 6 | 84.7% | 0.7% |

Example 10

A 500 ml separable flask equipped with a stirrer, a reflux condenser, a dropping funnel, and a thermometer was charged with 24.9 parts (0.1 mol) of triallyl isocyanurate, 2.95 parts (0.072 mol) of acetonitrile, 0.19 part (0.002 mol) of phenol, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 36.7 parts (0.3 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 70° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 4.

Example 11

The procedure of Example 10 was repeated except that the trimethoxysilane which was a starting material was replaced with triethoxysilane. The conversion rate and the production rate of the addition isomer are shown in Table 4.

Example 12

The procedure of Example 10 was repeated except that the trimethoxysilane which was a starting material was replaced with pentamethyldisiloxane. The conversion rate and the production rate of the addition isomer are shown in Table 4.

Example 13

A 500 ml separable flask equipped with a stirrer, a reflux condenser, a dropping funnel, and a thermometer was charged with 82.0 parts (1 mol) of 1,5-hexadiene, 19.7 parts (0.48 mol) of acetonitrile, 1.22 parts (0.013 mol) of phenol, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 244.4 parts (2 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 70° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 5.

Example 14

The procedure of Example 13 was repeated except that the trimethoxysilane which was a starting material was replaced with triethoxysilane. The conversion rate and the production rate of the addition isomer are shown in Table 5.

Example 15

The procedure of Example 13 was repeated except that the trimethoxysilane which was a starting material was replaced with pentamethyldisiloxane. The conversion rate and the production rate of the addition isomer are shown in Table 5.

Example 16

A 500 ml separable flask equipped with a stirrer, a reflux condenser, a dropping funnel, and a thermometer was charged with 104.0 parts (1 mol) of styrene, 19.7 parts (0.48 mol) of acetonitrile, 1.22 parts (0.013 mol) of phenol, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 122.2 parts (1 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 70° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 6.

Example 17

The procedure of Example 16 was repeated except that the trimethoxysilane which was a starting material was replaced with triethoxysilane. The conversion rate and the production rate of the addition isomer are shown in Table 6.

Example 18

The procedure of Example 16 was repeated except that the trimethoxysilane which was a starting material was replaced with pentamethyldisiloxane. The conversion rate and the production rate of the addition isomer are shown in Table 6.

Comparative Example 7

The procedure of Example 10 was repeated except that acetonitrile and phenol were not used. The conversion rate and the production rate of the addition isomer are shown in Table 4.

Comparative Example 8

The procedure of Example 10 was repeated except that acetonitrile and phenol were replaced with acetic acid. The conversion rate and the production rate of the addition isomer are shown in Table 4.

Comparative Example 9

The procedure of Example 13 was repeated except that acetonitrile and phenol were not used. The conversion rate and the production rate of the addition isomer are shown in Table 5.

Comparative Example 10

The procedure of Example 13 was repeated except that acetonitrile and phenol were replaced with acetic acid. The conversion rate and the production rate of the addition isomer are shown in Table 5.

Comparative Example 11

The procedure of Example 16 was repeated except that acetonitrile and phenol were not used. The conversion rate and the production rate of the addition isomer are shown in Table 6.

Comparative Example 12

The procedure of Example 16 was repeated except that acetonitrile and phenol were replaced with acetic acid. The conversion rate and the production rate of the addition isomer are shown in Table 6.

TABLE 4

|  | Conversion rate | Production rate of the addition isomer |
| --- | --- | --- |
| Example 10 | 92.5% | 0.9% |
| Example 11 | 90.1% | 0.5% |
| Example 12 | 91.1% | 0.3% |
| Comparative Example 7 | 35.3% | 1.6% |
| Comparative Example 8 | 86.6% | 5.6% |

TABLE 5

|  | Conversion rate | Production rate of the addition isomer |
| --- | --- | --- |
| Example 13 | 88.6% | 1.0% |
| Example 14 | 87.3% | 0.9% |
| Example 15 | 86.1% | 0.5% |
| Comparative Example 9 | 43.2% | 9.6% |
| Comparative Example 10 | 76.5% | 1.5% |

TABLE 6

|  | Conversion rate | Production rate of the addition isomer |
| --- | --- | --- |
| Example 16 | 91.1% | 0.2% |
| Example 17 | 89.9% | 0.6% |
| Example 18 | 88.8% | 0.6% |
| Comparative Example 11 | 1.6% | 0.9% |
| Comparative Example 12 | 84.7% | 0.7% |

Example 19

A 500 ml separable flask equipped with a stirrer, a reflux condenser, a dropping funnel, and a thermometer was charged with 24.9 parts (0.1 mol) of triallyl isocyanurate, 0.15 part (0.002 mol) of ammonium acetate, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 36.7 parts (0.3 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 80° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 7.

Example 20

The procedure of Example 19 was repeated except that the trimethoxysilane which was a starting material was replaced with triethoxysilane. The conversion rate and the production rate of the addition isomer are shown in Table 7.

Example 21

The procedure of Example 19 was repeated except that the trimethoxysilane which was a starting material was replaced with pentamethyldisiloxane. The conversion rate and the production rate of the addition isomer are shown in Table 7.

Example 22

A 500 ml separable flask equipped with a stirrer, a reflux condenser, a dropping funnel, and a thermometer was charged with 82.0 parts (1 mol) of 1,5-hexadiene, 1.0 part (0.013 mol) of ammonium acetate, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 244.4 parts (2 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 70° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 8.

Example 23

The procedure of Example 22 was repeated except that the trimethoxysilane which was a starting material was replaced with triethoxysilane. The conversion rate and the production rate of the addition isomer are shown in Table 8.

Example 24

The procedure of Example 22 was repeated except that the trimethoxysilane which was a starting material was replaced with pentamethyldisiloxane. The conversion rate and the production rate of the addition isomer are shown in Table 8.

Example 25

A 500 ml separable flask equipped with a stirrer, a reflux condenser, a dropping funnel, and a thermometer was charged with 104.0 parts (1 mol) of styrene, 1.0 part (0.013 mol) of ammonium acetate, and toluene solution of the platinum complex of the amount corresponding to 0.00005 mol of the platinum complex in relation to 1 mol of trimethoxysilane which was added dropwise in the subsequent step, and the mixture was stirred. The mixture was then heated, and when the internal temperature reached 60° C., 122.2 parts (1 mol) of the trimethoxysilane was added dropwise for 1 hour. The reaction started simultaneously with the start of the dropwise addition, and since the temperature of the reaction mixture gradually increased from 60° C., heating was ceased, and the dropwise addition was continued with the temperature regulated not to exceed 70° C. After the completion of the dropwise addition, the reaction mixture was aged for 1 hour with the internal temperature maintained at 70° C. by heating. The content was then analyzed by gas chromatography. The conversion rate and the production rate of the addition isomer are shown in Table 9.

Example 26

The procedure of Example 25 was repeated except that the trimethoxysilane which was a starting material was replaced with triethoxysilane. The conversion rate and the production rate of the addition isomer are shown in Table 9.

Example 27

The procedure of Example 25 was repeated except that the trimethoxysilane which was a starting material was replaced with pentamethyldisiloxane. The conversion rate and the production rate of the addition isomer are shown in Table 9.

Comparative Example 13

The procedure of Example 19 was repeated except that ammonium acetate was not used. The conversion rate and the production rate of the addition isomer are shown in Table 7.

Comparative Example 14

The procedure of Example 19 was repeated except that ammonium acetate was replaced with acetic acid. The conversion rate and the production rate of the addition isomer are shown in Table 7.

Comparative Example 15

The procedure of Example 22 was repeated except that ammonium acetate was not used. The conversion rate and the production rate of the addition isomer are shown in Table 8.

Comparative Example 16

The procedure of Example 22 was repeated except that ammonium acetate was replaced with acetic acid. The conversion rate and the production rate of the addition isomer are shown in Table 8.

Comparative Example 17

The procedure of Example 25 was repeated except that ammonium acetate was not used. The conversion rate and the production rate of the addition isomer are shown in Table 9.

Comparative Example 18

The procedure of Example 25 was repeated except that ammonium acetate was replaced with acetic acid. The conversion rate and the production rate of the addition isomer are shown in Table 9.

TABLE 7

|  | Conversion rate | Production rate of the addition isomer |
|---|---|---|
| Example 19 | 94.7% | 0.6% |
| Example 20 | 95.3% | 0.9% |
| Example 21 | 92.1% | 0.2% |
| Comparative Example 13 | 35.3% | 1.6% |
| Comparative Example 14 | 86.6% | 5.6% |

TABLE 8

|  | Conversion rate | Production rate of the addition isomer |
|---|---|---|
| Example 22 | 91.2% | 0.3% |
| Example 23 | 91.9% | 0.2% |
| Example 24 | 91.1% | 0.4% |

TABLE 8-continued

|  | Conversion rate | Production rate of the addition isomer |
|---|---|---|
| Comparative Example 15 | 43.2% | 9.6% |
| Comparative Example 16 | 76.5% | 1.5% |

TABLE 9

|  | Conversion rate | Production rate of the addition isomer |
|---|---|---|
| Example 25 | 94.1% | 0.2% |
| Example 26 | 90.3% | 0.4% |
| Example 27 | 89.9% | 0.1% |
| Comparative Example 17 | 1.6% | 0.9% |
| Comparative Example 18 | 84.7% | 0.7% |

The results of the Examples and Comparative Examples as described above reveal that the present invention is capable of producing the compound having the olefin terminal carbon atom silylated at a high efficiency without sacrificing the hydrosilylation reactivity while suppressing the generation of the by-product addition isomer.

Japanese Patent Application Nos. 2010-274710, 2010-274730 and 2010-274745 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A hydrosilylation method wherein
(i) an olefin compound having a carbon-carbon unsaturated bond selected from the group consisting of: an olefin compound selected from the group consisting of allyl isocyanate, triallyl isocyanurate, 1,3-butadiene, isoprene, 1,4-pentadiene, 1,5-hexadiene, 1,6-heptadiene, 1,7-octadiene, 1,8-nonadiene, 1,9-decadiene, divinylcyclohexane, trivinylcyclohexane, diallylcyclohexane, triallylcyclohexane, styrene, allyl benzene, and allyl phenol; a diene compound of formula (4):

$$CH_2=C(R^4)-(CH_2)_m-C(R^4)=CH_2 \quad (4)$$

wherein $R^4$ is independently hydrogen atom or a monovalent hydrocarbon group and m is an integer of 0 to 20; and a compound containing an aliphatic ring structure and/or an aromatic ring structure having vinyl group or allyl group, and
(ii) a compound having a hydrogensilyl group selected from the group consisting of hydrogentrimethoxysilane, hydrogenmethyldimethoxysilane, hydrogendimethylmethoxysilane, hydrogentriethoxysilane, hydrogenmethyldiethoxysilane, hydrogendimethylethoxysilane, hydrogentri(2-propenoxy)silane, hydrogenmethyldi(2-propenoxy)silane, hydrogendimethyl(2-propenoxy)silane, organopolysiloxane and organosilsesquioxane having a hydrosilyl group produced by hydrolytic condensation of one of said silane monomers, 1,3,5,7-tetramethyltetrasiloxane, 1,1,3,3-tetramethyldisiloxane, pentamethyldisiloxane, and dimethyl silicone polymer containing 3 to 100 silicon atoms having a hydrosilyl group on its side chain or at its terminal are reacted in the presence of an organoammonium salt compound of formula (5):

$$R^5-[C(=O)O^-.NR^6_4{}^+]_h \quad (5)$$

wherein $R^5$ is an h-valent hydrocarbon group containing 1 to 20 carbon atoms, $R^6$ is independently a hydrogen atom or a monovalent hydrocarbon group containing 1 to 6 carbon atoms, and h is 1 or 2 by using catalytic action of platinum and/or its complex compound to form a hydrosilylated derivative of said olefin compound.

2. The hydrosilylation method of claim 1, wherein the olefin compound is selected from the group consisting of allyl isocyanate and triallyl isocyanurate.

3. The hydrosilylation method of claim 1, wherein the compound having a hydrogensilyl group (ii) is used in an amount of 0.7 to 1.5 mol in relation to 1 mol of the unsaturated group of the olefin compound (i).

4. The hydrosilylation method of claim 1, wherein the reaction is conducted at a temperature of from 50 to 150° C. for from 10 to 300 minutes.

5. The hydrosilylation method of claim 1, wherein the platinum and/or its complex compound are those having an oxidation number of Pt(0) or Pt(II).

6. The hydrosilylation method of claim 1, comprising the following sequential steps:
(1) mixing together and stirring 0.1 mol of triallyl isocyanurate, 0.002 mol of ammonium acetate, and a toluene solution of a platinum complex in an amount corresponding to 0.00005 mol of the platinum complex in relation to 1 mol of the trimethoxysilane to be added in step (3);
(2) heated the mixture formed in step (1) to a temperature of 60° C.;
(3) adding 0.3 mol of trimethoxysilane dropwise to said mixture over a period of 1 hour while regulating the temperature to not exceed 80° C.; and
(4) aging the reaction mixture resulting from step (3) for 1 hour at a temperature of 70° C.

* * * * *